(12) United States Patent
Ahn

(10) Patent No.: US 6,676,291 B2
(45) Date of Patent: Jan. 13, 2004

(54) APPARATUS FOR MEASURING DENSITY OF BONE

(75) Inventor: Young Bok Ahn, Seoul (KR)

(73) Assignee: Osteosys Co., Ltd., Seoul (KR)

( * ) Notice: Subject to any disclaimer, the term of this patent is extended or adjusted under 35 U.S.C. 154(b) by 90 days.

(21) Appl. No.: 10/010,799

(22) Filed: Dec. 7, 2001

(65) Prior Publication Data

US 2003/0068014 A1 Apr. 10, 2003

(30) Foreign Application Priority Data

Sep. 10, 2001 (KR) .......................... 2001-55510

(51) Int. Cl.[7] ................................. H05G 1/00
(52) U.S. Cl. ................... 378/208; 378/68; 378/54; 378/50
(58) Field of Search ................... 378/208, 68, 54, 378/50; 601/27, 40; 600/587, 592, 595

(56) References Cited

U.S. PATENT DOCUMENTS 5,136,743 A * 8/1992 Pirela-Cruz ................ 5/647
5,479,471 A * 12/1995 Buckland .................. 378/208
5,748,704 A   5/1998 Mazess et al. .............. 378/54
6,252,928 B1 * 6/2001 MacKenzie ................. 378/54
6,282,258 B1 * 8/2001 Stein et al. ................. 378/54
6,315,445 B1 * 11/2001 Mazess et al. ............. 378/196

* cited by examiner

Primary Examiner—Edward J. Glick
Assistant Examiner—Elizabeth Gemmell
(74) Attorney, Agent, or Firm—Morgan & Finnegan, L.L.P.

(57) ABSTRACT

The present invention discloses an (x-ray) bone densitometer comprising a stand including an "L"-shape handle consisting of an a horizontal and a vertical plate capable of rotating between an horizontal position and a vertical position on the horizontal plate, a handle groove, a first guide pin and a second guide pin, and a stand groove; and a housing including an opening formed perpendicular in the center of the upper part (of said housing), the opening having one or more of the first and the second guide grooves for guiding the movements of first and said second guide pins, a stand settle groove for settling the stand when the stand is settled horizontally, and a stand erecting groove for supporting the stand when the stand is erected in slope.

5 Claims, 9 Drawing Sheets

[Fig. 1a] PRIOR ART
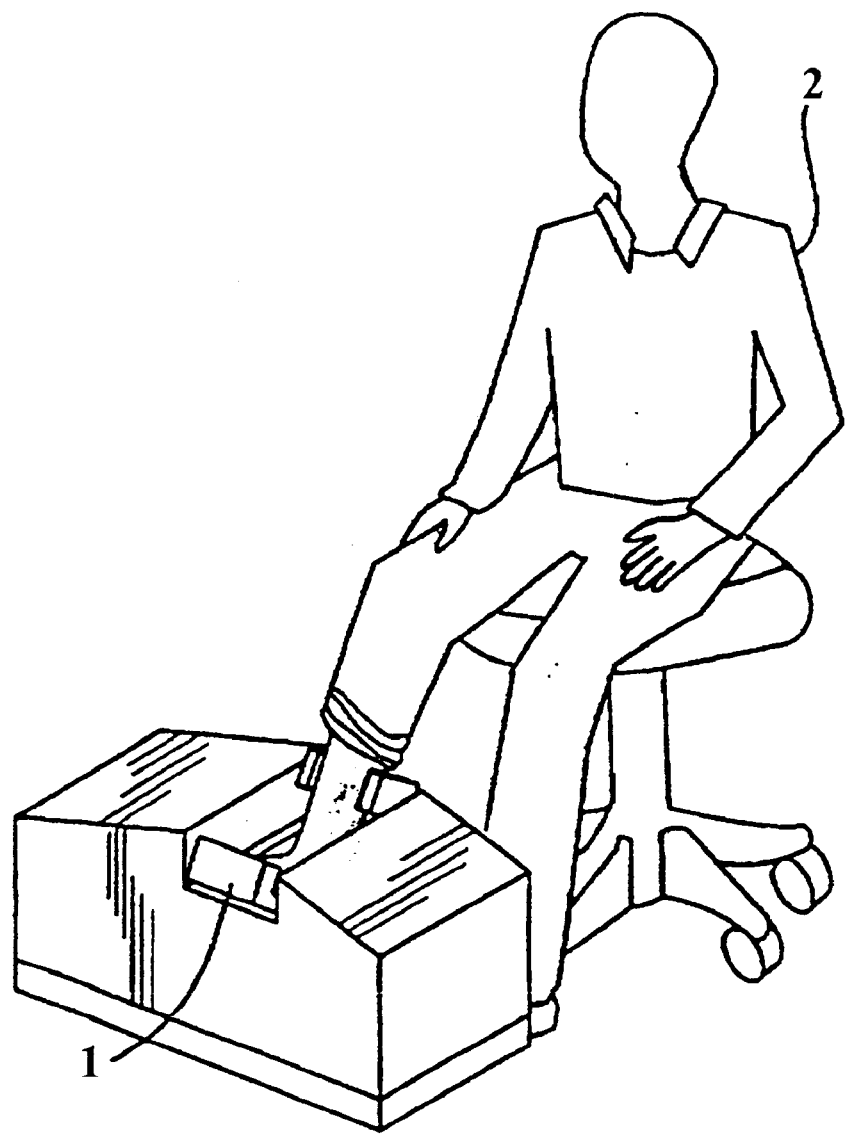

[Fig. 1b] PRIOR ART
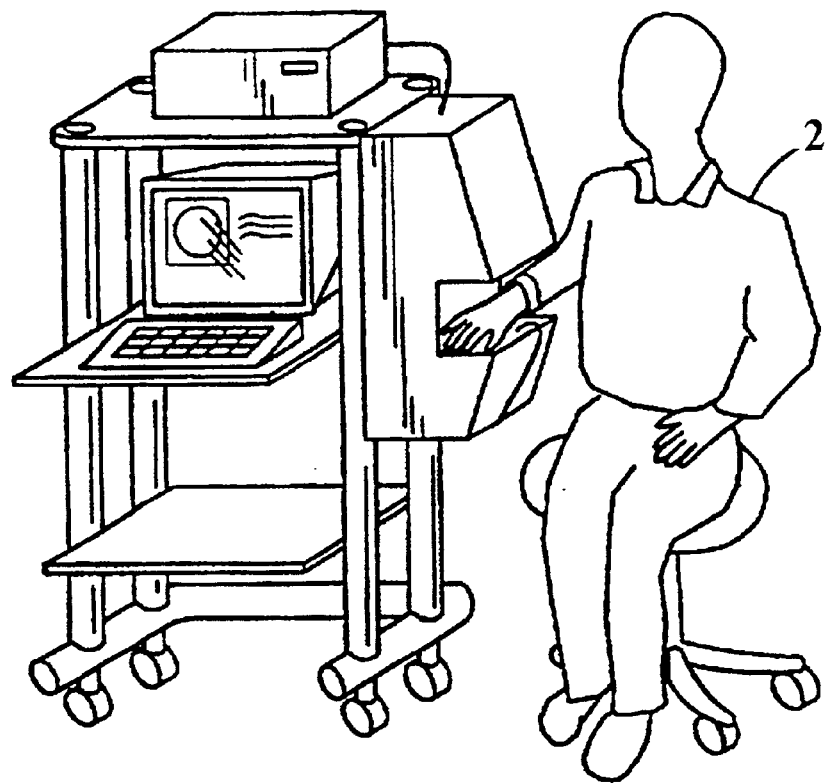
[Fig. 2]
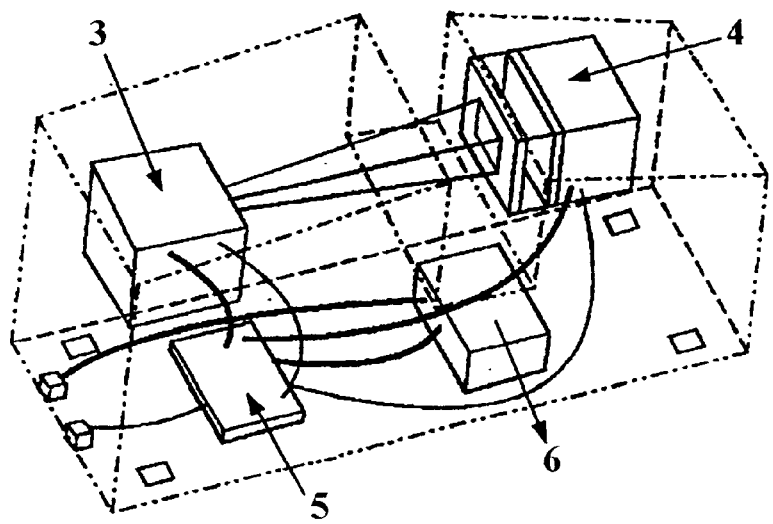

[Fig. 3a]
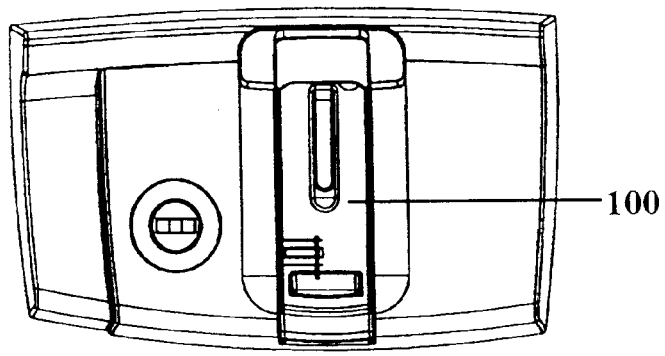
[Fig. 3b]
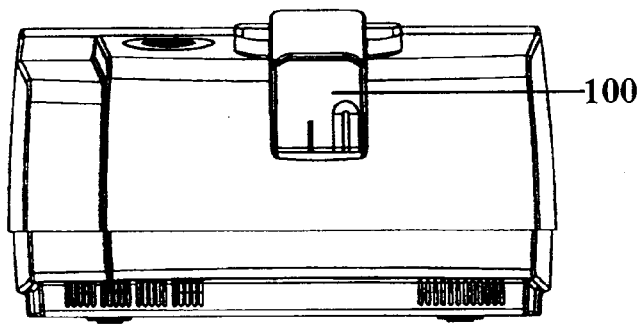
[Fig. 3c]
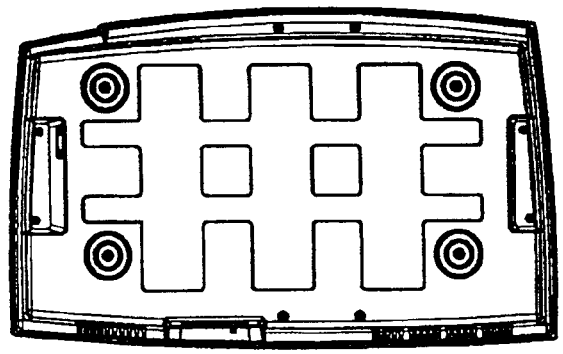

[Fig. 3d]
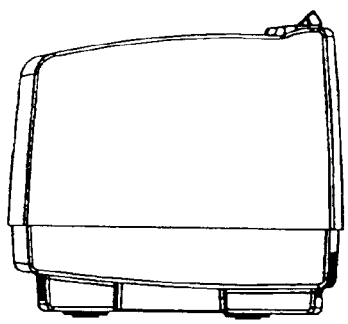
[Fig. 3e]
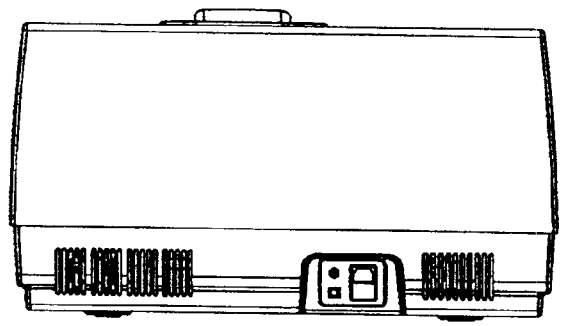
[Fig. 3f]
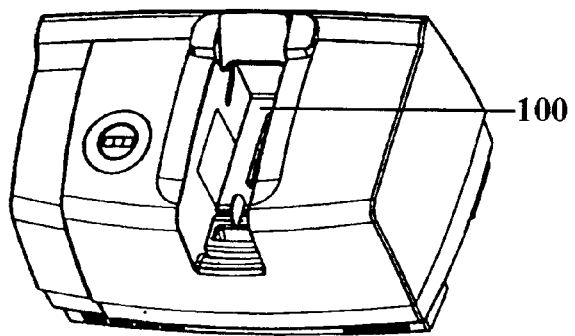

[Fig. 4a]
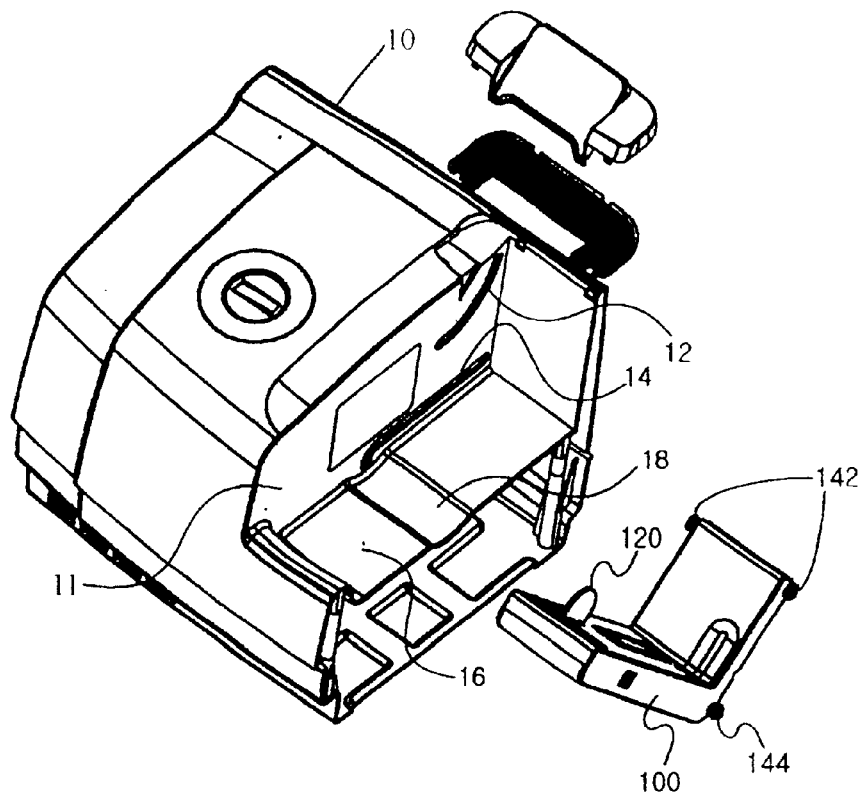
[Fig. 4b]
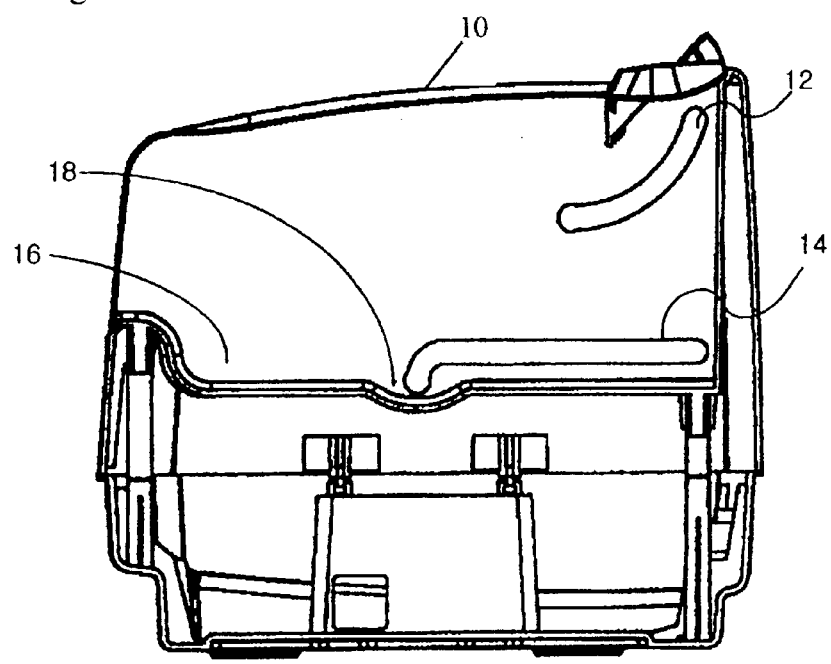

[Fig. 5a]
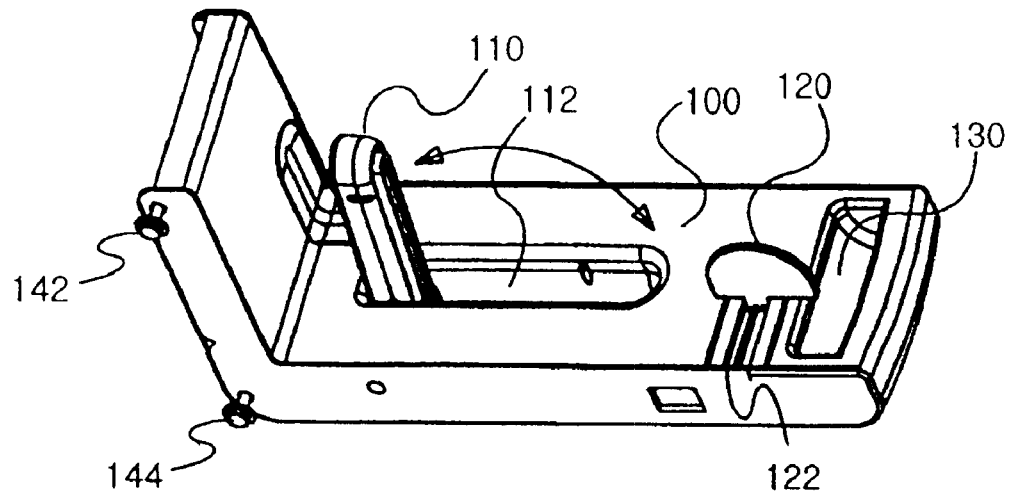
[Fig. 5b]
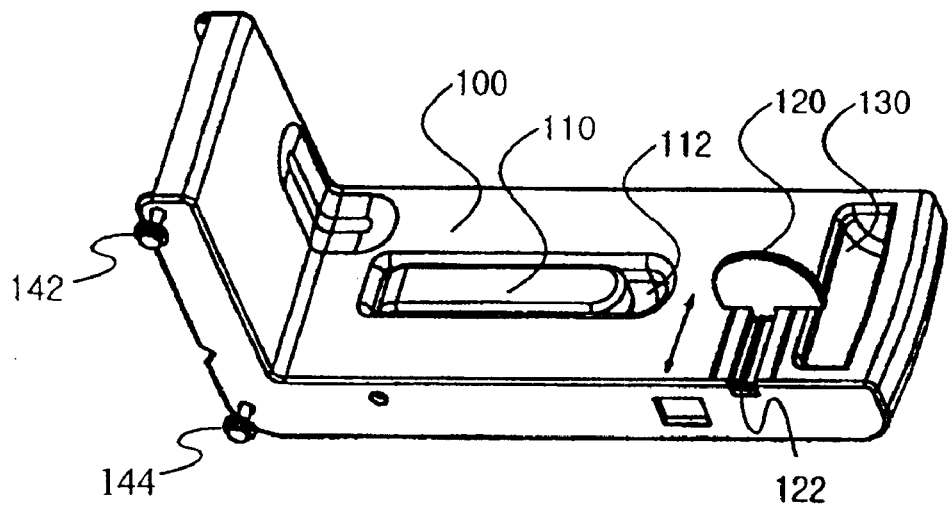

[Fig. 5c]
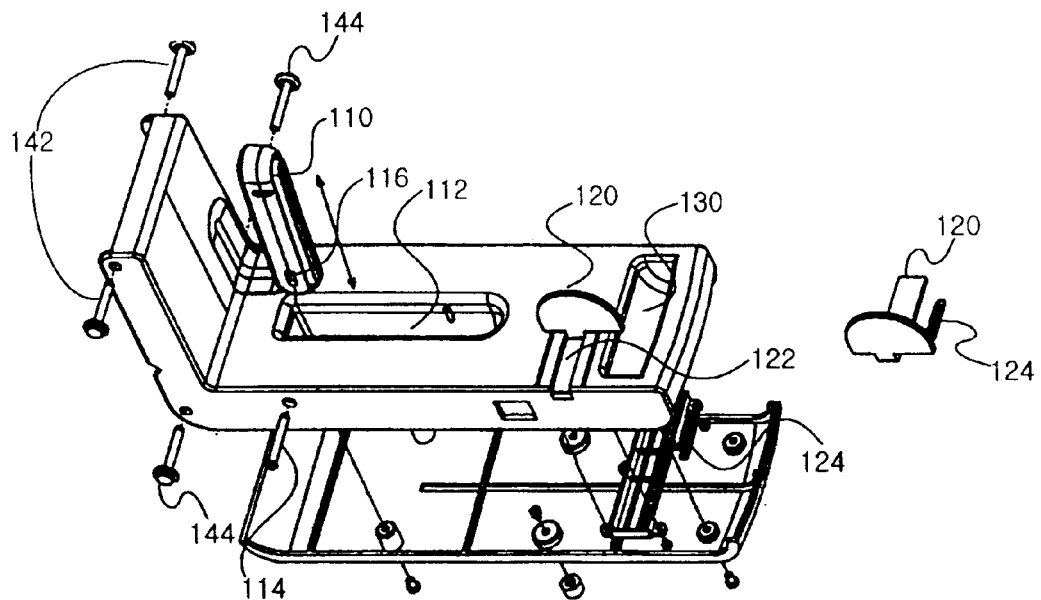
[Fig. 6a]
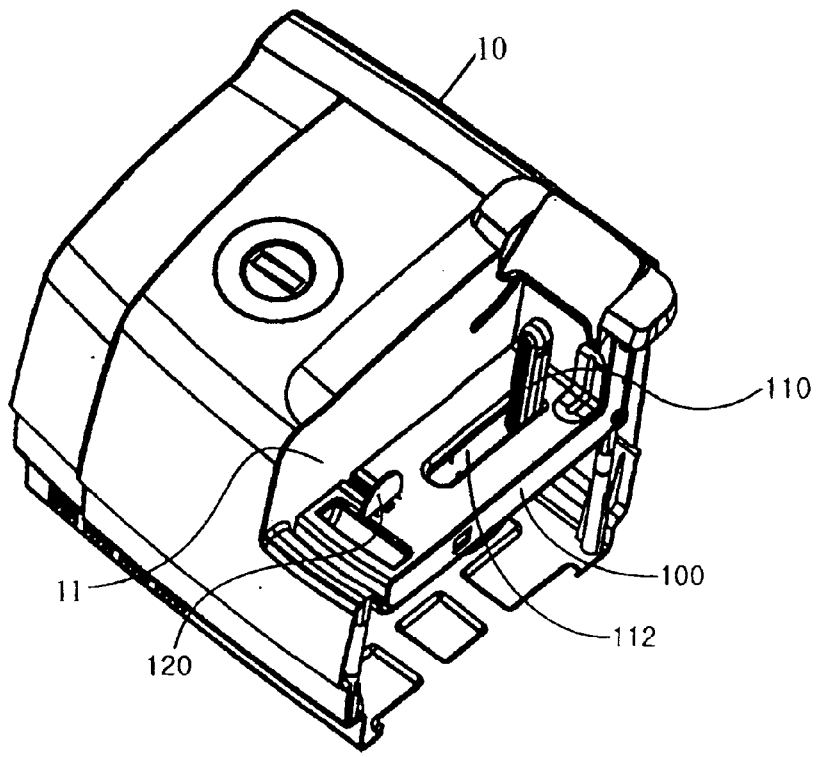

[Fig. 6b]
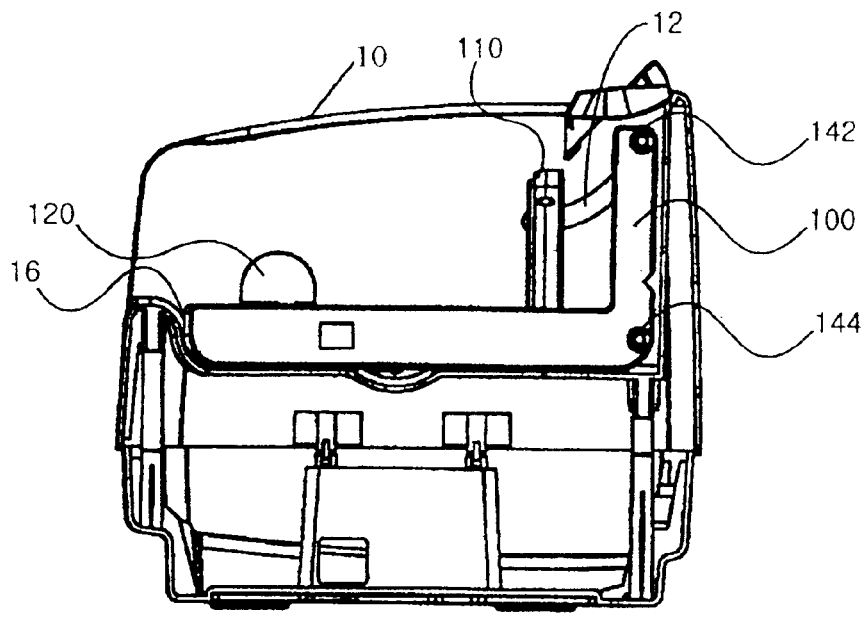
[Fig. 6c]
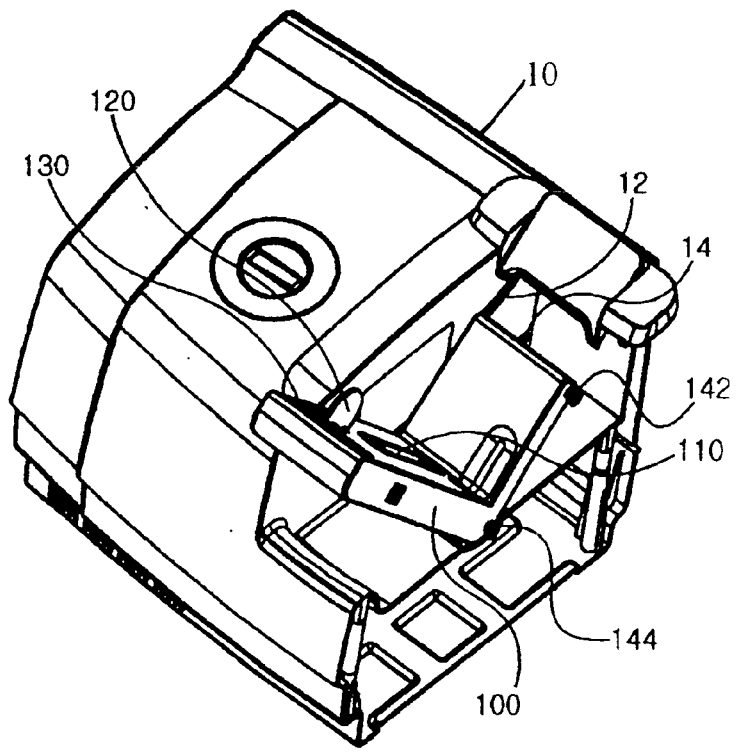

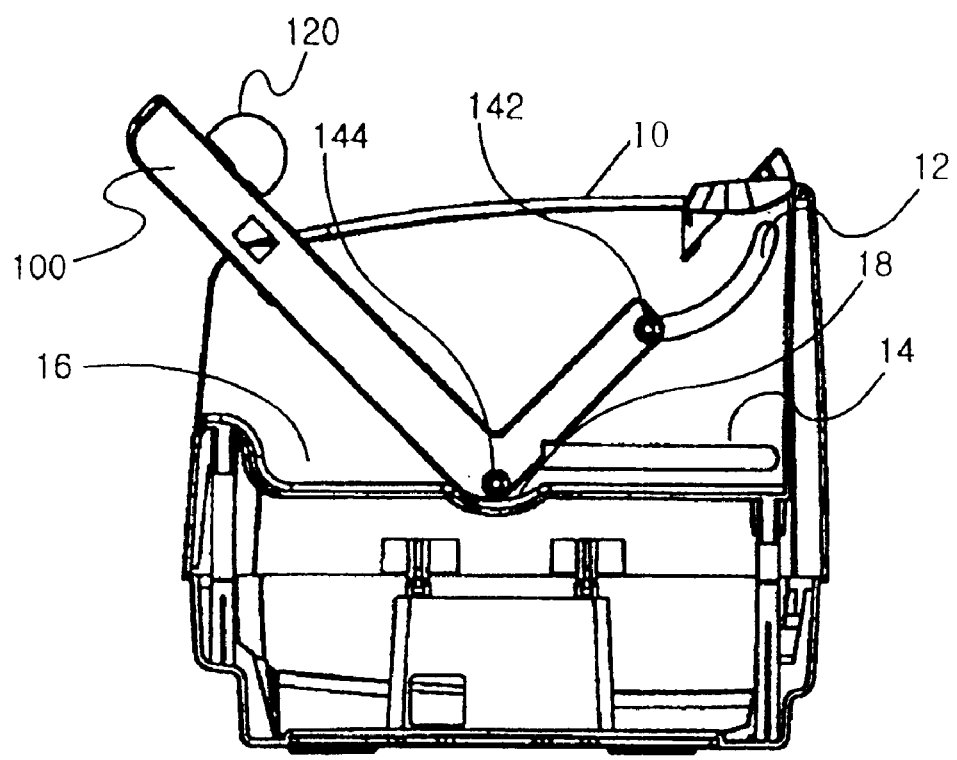
[Fig. 6d]

APPARATUS FOR MEASURING DENSITY OF BONE

FIELD OF THE INVENTION

The present invention relates generally to a bone densitometer for measuring bone density for the purpose of diagnosis of osteoporosis using x-ray, and, in particular, to an integrated bone densitometer having a stand for supporting the part of a body to be measured which is so designed that the position of the stand can be adjusted.

DESCRIPTION OF THE PRIOR ART

Generally, density of a human bone decreases with increase of the age as it can be observed from a cross-sectional view of a bone showing devastation by pore formations in the tissue of the bone, resulting in decrease of the bone strength. When the density of a bone decreases, the bone can easily be injured by small impact and, in extreme cases, even a patient's life can be menaced. A bone densitometer is an apparatus for measuring the density of a bone for the purpose of preventing or stopping this decrease process in bone density.

For obtaining an accurate result, it is preferable that the bones of the heel or of the wrist of a patient are measured, and measurement of the same bone should be repeated for monitoring the process of osteoporosis.

As shown in FIG 1a, a conventional bone densitometer is equipped with a foot stand 1 for accurate measurement of heel bones, comprising a sole guide and a calf guide capable of pivoting to form a right angle during the measurement. A patient 2 puts his sole and heel on the sole guide and the calf guide, respectively, while the sole guide and the calf guide remain rectangular to each other during the measurement.

Referring to FIG. 1b, in order to measure the density of wrist bones, the foot stand 1 should be removed from the bone densitometer. If, on the other hand, a measurement of heel bones is necessary after measurement of wrist bones, the foot stand 1 should be reinstasted and the position and direction of the bone densitometer need to be rearranged, which process is unhandy and inconvenient.

SUMMARY OF THE INVENTION

The present invention, conceived in view of the above demand, alms to provide a bone densitometer with a stand which is capable of measuring bone density of both the wirst bones and the heel bones by simply adjusting the settle position according to the body parts to be measured The present invention further aims to provide a stand for bone densitometer which allows easy change of the settle position for different body parts in order to yield enhanced convenience in measurements.

BRIEF DESCRIPTION OF THE DRAWINGS

FIG. 1a illustrates a conventional bone densitometer in use for measuring the heel part.

FIG. 1b illustrates a conventional bone densitometer in use for measuring the wrist part.

FIG. 2 is a schematic drawing showing the construction of a bone densitometer in accordance with the present invention.

FIGS. 3a through 3f illustrate the outer appearances of a bone densitometer having a stand 100 for support of the body part to be measured as set horizontally, wherein FIG. 3a is a plane view, FIG. 3b is a front view, FIG. 3c is a bottom view, FIG. 3d is a right side view. FIG. 3e is a rear view, and FIG. 3f is a perspective view.

FIG. 4a is a perspective view of a bone densitometer as the right part cut off, and of the stand 100 as it is separated from the main body of the bone densitometer.

FIG. 4b is a cross sectional view of the bone densitometer as the right part cut off, after the stand 100 has been separated.

FIG. 5a is a perspective view of the stand 100 with a handle 110 in perpendicular position.

FIG. 5b is a perspective view of the stand 100 with a handle 110 in horizontal position.

FIG. 5c is an exploded perspective view of the stand.

FIG. 6a is a perspective view of a bone densitometer in accordance with the present invention with its stand set horizontally, and the right side of the stand being cut off.

FIG. 6b is a right side view of a bone densitometer in accordance with the present invention with its stand set horizontally, and the right side of the stand being cut off FIG. 6c is a perspective view of a bone densitometer in accordance with the present invention with its stand erected to a slope position, and the right side of the stand being cut off.

FIG. 6d is a cross sectional view of a bone densitometer in accordance with the present invention with its stand erected to a slope position, and the right side of the stand being cut off.

DETAILED DESCRIPTION OF THE PREFERRED EMBODIMENTS

Now, a description of the preferred embodiment of the present invention is given below, making reference to the accompanying drawings.

FIG. 2 is a schematic drawing showing the construction of a bone densitometer in accordance with the present invention.

Referring to FIG. 2, the bone densitometer comprises an x-ray generator 3, an x-ray detector 4, a power supply 5, and a main board 6.

The x-ray generator 3 includes a controller, a D/A converter, a driver, a collimator A for preventing dispersion of x-ray, and a shutter for physical interception of x-ray. The x-ray dector 4 which receives the x-rays from the x-ray generator 3, includes a scintillator for changing the x-ray to a visible ray. The power supply 5 supplies electricity securely to the x-ray generator 3, the x-ray dector 4, and the main board 6, the main board 6 controls the x-ray generator 3 and the x-ray dector 4, and transmits images received from the x-ray dector 4 through USB (Universal Serial Bus).

FIGS. 3a through 3f illustrate the outer appearances of the bone densitometer having a stand 100 for support of the body part to be measured as set horizontally, wherein FIG. 3a is a plane view, FIG. 3b is a front view, FIG. 3c is a bottom view, FIG. 3d is a right side view, FIG. 3e is a rear view, and FIG. 3f is a perspective view.

FIGS. 4a and 4b show the bone densitometer with the right part cut off.

FIG. 4a is a perspective view of the bone densitometer as the right part cut off, and of the stand 100 as it is separated from the main body of the bone densitometer.

As shown in FIG. 4a, a housing 10 includes an opening 11 formed perpendicular in the center of the upper part and having the first guide groove 12 and the second guide groove 14 at each side of the opening 11 for guiding the movements of the stand 100; a stand settle groove 16 formed concavely in the bottom of the opening 11 for accommodating the stand 100 when the stand 100 is settled horizontally; and a stand erecting groove 18 formed concavely to support the stand 100 when the stand 100 the stand 100 is erected in slope.

And at far right side of FIG. 4a, the stand 100 for supporting the measure part of the body is shown as separated from the housing 10. The stand 100 includes the first guide pin 142 to be connected to the first guide groove 12 and the second guide pin 144 to be connected to the second guide groove 14 at each side in order to ensure safe guidance of the movements of the stand 100 in the opening 11.

FIG. 4b is a cross sectional view of the bone densitometer as the right part cut off, after the stand 100 has been separated.

Referring to FIG. 4b, the first guide grooves 12 are formed to enable curve motion between the inner lower part and the outer upper part of the opening 11 in combination with the first guide pins 142 of the stand 100, while the second guide grooves 14 comprise a linear part for guiding linear motion of the second guide pins 144 along each side of the opening 11, and a curved part at the innermost end of the linear part to allow the second guide pins 144 to move downward. And, the stand settle groove 16 includes a stand erecting groove 18 formed concavely for supporting edge of the stand 100.

FIG. 5a is a perspective view of the stand 100 with a handle 110 in perpendicular position.

Referring to FIG. 5a, the stand 100 in 'L'-shape consisted of a horizontal plate and a vertical plate includes a handle 110 rotatable between horizontal and vertical angles on the horizontal plate; a handle groove 112 formed on the horizontal plate for accommodating the handle 110 in the horizontal plate when the handle 110 is rotated to the horizontal position; the first guide pins 142 and the second guide pins 144 formed at each side of the stand 100 for guiding movements of the stand 100; a support plate 120 formed in plate form vertically to the horizontal plate; and a stand groove 130 formed at an end of the stand 100, allowing easy grasping and carrying of the horizontal plate. Thus, a simple holding of the handle 110 in its vertical position allows correct placing of the wrist part to be measured and supporting thereof at the same time, so that the accuracy of measurement is ensured.

FIG. 5b is a perspective view of the stand 100 with the handle 110 in horozontal position.

If the handle 110 is in its horizontal position, laid in the handle groove 112 as shown in FIG. 5b, the heel bones can be measured, in which case the calf shall adhere to the horizontal plate while the sole shall adhere to the vertical plate.

The parts of the stand 100 are explained below with reference to FIG. 5c, which is an exploded view thereof.

As shown in FIG. 5c, the handle 110 includes a shaft hole 116 in a slot form formed along the handle's length, piercing the lower part of the handle 110, and turns on the shaft 114 which pierces the side of the stand 100 and inserts into the shaft hole 116. When the handle 110 is set vertically, the handle 110 goes down until the shaft 114 touches the upper end of the shaft hole 116, and is set not to rotate further, because the lower part of the handle 110 is blocked by the handle groove 112. And, when the handle 110 is to be set horizontally, the handle 110 should be raised until the shaft 114 touches the lower end of the shaft hole 116 and then be pivoted on the shaft 114 until the handle 114 is entirely buried in the handle groove 112.

The support plate 120 is combined with the support plate slot 122 in a manner movable along the support plate slot 122 formed on the horizontal plate of the stand 100 in a direction rectangular to the length of the stand 100. The support plate 120 initially remains tightly drawn to the inside of the support plate slot 122 by the restore spring 124. When measuring commences, the support plate is moved outward along the support plate 122, the measuring part is placed on the stand 100, so that the measuring part is supported and tightly adhered to the support plate 120 by force of the restore spring 124 after the force inflicted on the support plate 122 has been removed. In addition, the far right drawing in FIG. 5c illustrates the support plate 120 and the restore spring 124 as combined together.

FIG. 6a is a perspective view of a bone densitometer in accordance with the present invention with its stand set horizontally, and the right side of the stand being cut off.

A bone densitometer with the stand set horizontally in the opening 11, and with vertically erected handle 110 in the stand 100 as shown in FIG. 6a, is for measuring the wrist bones. When a patient puts his hand in the opening 11 and grasps the handle 110, the forearm is properly supported by the support plate 100 and the wrist is correctly placed in the pathway of the x-ray.

FIG. 6b is a right side view of a bone densitometer in accordance with the present invention with its stand set horizontally, and the right side of the stand being cut off.

Referring to FIG. 6b, when the stand 100 is set horizontally, the first guide pin 142 is situated at the upper end of the first guide groove 12, the second guide pin 144 is situated at the right end of the second guide groove (not illustrated in the drawing), and the stand 100 is settled on the stand settle groove 16. Then, the stand 100 is supported firmly without any additional fixture means because the bottom and edge of the stand 100 contact tightly to the surface of the bottom and sides of the stand settle groove 16.

FIG. 6c is a perspective view of a bone densitometer in accordance with the present invention with its stand erected to a slope position, and the right side of the stand being cut off.

If the user grasps the stand groove 130 and lifts the stand 100, while pulling it in a state as in FIG. 6a, so that the first guide pin 142 is situated at the lower end of the first guide groove 12 and the second guide pin 144 is situated at the left end of the second guide groove 14, the edges of the stand 100 are settled on the stand erection groove 18 in slope as shown in FIG. 6c. This structure of the bone densitometer is designed for measurement of the heel bones. For measuring density of the heel bones, the handle 110 is laid down and put into the horizontal plate of the stand 100, and then the heel is put in the pathway of the x-ray by adherences of the calf to the horizontal plate and of the sole to the vertical plate.

FIG. 6d is a cross sectional view of a bone densitometer in accordance with the present invention with its stand erected to a slope position, and the right side of the stand being cut off.

If the user grasps the stand groove 130 and lifts the stand 100 while pulling it in a state as in FIG. 6b, the first guide pin 142 moves in curve to the inner lower part of the densitometer along the first guide groove 12 and the second guide pin 144 enters the curved part of the second guide groove 14 and moves downward so that the edges of the stand 100 also move downward, and thus, the stand 100 is settled on the stand erection groove 18 forming a 'V'-shape, as shown in FIG. 6d. With the stand 100 settled as in FIG.

6d, the second guide pin 144 is positioned in the lower end of the curved part of the second guide groove 14 and the stand 100 is not movable to the right, to the left, or to downward, so that the stand is supported firmly without any additional fixing means.

In order to change the position of the stand 100 from a status as in FIG. 6d to a status as in FIG. 6b, the stand should be lifted, to let the second guide pin 144 depart the lower end of the curved part of the second guide groove 14, and then the first guide pin 142 is moved to the outer upper end of the first guide groove 12, while the second guide pin 144 is moved to the outer end of the second guide groove 14, so that the stand 100 is settled on the stand settle groove 16 horizontally.

Although the present invention has been described above with reference to the preferred embodiments, the scope of the rights of the subject invention is not restricted thereto, but rather shall be determined by the claims attached herein below and their equivalents, allowing various alterations, modifications, and adjustments, as those skilled in the art will understand.

As described above, the present invention allows easy measurements of both heel bones and wrist bones without additional apparatus, because the bone densitometer in accordance with the present invention is equipped with a stand capable of supporting a foot as well as a wrist.

Further, since the bone densitometer in accordance with the present invention is equipped with an integrated stand capable of changing its position and capable of supporting the wrist part in horizontal, or supporting the heel parting slope position, the bone densitometer enhances convenience in measurements of the bone density.

What is claimed is:

1. A bone densitometer having an opening between an x-ray generator and an x-ray detector comprising:

a stand in an "L"-shape consisting of a horizontal plate and a vertical plate including a handle capable of rotating between a horizontal position and a vertical position on said horizontal plate, a handle groove formed on said horizontal plate for accommodating said handle in said horizontal plate when said handle is positioned horizontally, a first guide pin and a second guide pin formed at each side of said stand for guiding the movements of said horizontal plate and vertical plate, and a stand groove formed at one end of said horizontal plate for grasping and carrying said horizontal plate; and a housing including an opening formed perpendicular in the center of the upper part of said housing, the opening having one or more of a first guide groove and a second guide groove at each side of said opening; a stand settle groove formed concavely in the bottom of said opening to accommodate said stand when said stand is settled horizontally; and a stand erecting groove formed concavely in said stand settle groove for supporting the edge of said stand when said stand is erected in slope.

2. A bone densitometer as set forth in claim 1, wherein said handle is bar-shaped and comprises a shaft hole piercing the lower part of said handle, and a shaft inserted in said shaft hole through the side of the stand.

3. A bone densitometer as set forth in claim 1, wherein said first guide grooves are formed between the inner low part and the outer upper part of said opening in the shape of a curve in order to guide the motion of said first guide pins.

4. A bone densitometer as set forth in claim 1, wherein said second guide grooves comprise:

a linear part for guiding said second pins' linear horizontal movements along each side of said opening; and a curved part at the innermost end of the linear part in order to allow the second guide pins to move downward.

5. A bone densitometer as set forth in claim 1, wherein said stand further comprises a support plate which is connected to the inside of the horizontal plate by a restore spring and moves in the perpendicular direction along the length of said horizontal plate.

* * * * *